(12) United States Patent
Qurishi et al.

(10) Patent No.: US 9,572,939 B2
(45) Date of Patent: Feb. 21, 2017

(54) PISTON FOR A CARTRIDGE FOR USE IN A DRUG DELIVERY DEVICE

(71) Applicant: SANOFI-AVENTIS DEUTSCHLAND GMBH, Frankfurt (DE)

(72) Inventors: Ramatullah Qurishi, Frankfurt am Main (DE); Martin Otten, Frankfurt am Main (DE); Stefan Trinkle, Frankfurt am Main (DE); Jörn Möckel, Frankfurt am Main (DE); Sebastian Thiel, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 199 days.

(21) Appl. No.: 14/355,617

(22) PCT Filed: Nov. 1, 2012

(86) PCT No.: PCT/EP2012/071648
§ 371 (c)(1),
(2) Date: May 1, 2014

(87) PCT Pub. No.: WO2013/064590
PCT Pub. Date: May 10, 2013

(65) Prior Publication Data
US 2014/0303567 A1  Oct. 9, 2014

(51) Int. Cl.
*A61M 5/315* (2006.01)
*A61M 5/31* (2006.01)

(52) U.S. Cl.
CPC .......... *A61M 5/315* (2013.01); *A61M 5/3129* (2013.01); *A61M 5/31511* (2013.01); *A61M 5/31513* (2013.01); *A61M 2005/31516* (2013.01); *A61M 2205/3569* (2013.01); *A61M 2205/60* (2013.01); *A61M 2205/6054* (2013.01)

(58) Field of Classification Search
CPC .............. A61M 5/315; A61M 5/31511; A61M 5/31513; A61M 2005/31516
See application file for complete search history.

(56) References Cited

U.S. PATENT DOCUMENTS

| 4,543,093 A | 9/1985 | Christinger | |
|---|---|---|---|
| 2003/0233075 A1* | 12/2003 | Huegli | A61M 5/31513 604/222 |
| 2005/0197626 A1* | 9/2005 | Moberg | A61M 5/14566 604/131 |

FOREIGN PATENT DOCUMENTS

| EP | 2407195 A1 | 1/2012 |
|---|---|---|
| JP | 2007532181 A | 11/2007 |
| WO | 7901111 A1 | 12/1979 |
| WO | 2005099793 A1 | 10/2005 |
| WO | 2010133675 A1 | 11/2010 |

(Continued)

*Primary Examiner* — Nathan R Price
*Assistant Examiner* — Melissa A Snyder
(74) *Attorney, Agent, or Firm* — McDonnell Boehnen Hulbert & Berghoff LLP

(57) ABSTRACT

The present invention relates to a piston for a cartridge to be filled with a medicament, the piston comprising: a first piston member comprising a first material and forming a distal end face of the piston, a second piston member comprising a second material of lower compressibility compared to the first material, wherein the second piston member is arranged in a cupped receptacle of the first piston member and provides a thrust receiving surface at a proximal end of the piston.

11 Claims, 2 Drawing Sheets

(56) References Cited

FOREIGN PATENT DOCUMENTS

| WO | 2010133676 A1 | 11/2010 |
|---|---|---|
| WO | 2011026932 A1 | 3/2011 |

\* cited by examiner

PISTON FOR A CARTRIDGE FOR USE IN A DRUG DELIVERY DEVICE

CROSS REFERENCE TO RELATED APPLICATIONS

The present application is a U.S. National Phase Application pursuant to 35 U.S.C. §371 of International Application No. PCT/EP2012/071648 filed Nov. 1, 2012, which claims priority to European Patent Application No. 11187479.8 filed Nov. 2, 2011. The entire disclosure contents of these applications are herewith incorporated by reference into the present application.

FIELD OF INVENTION

The present invention relates to a piston for a cartridge at least partially filled with a medicament. In particular, the invention relates to pistons that serve as a seal for tubular shaped cartridges to be used in drug delivery devices such like pen-type injectors.

BACKGROUND

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where a medicament is administered on a regular or irregular basis over a short term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose.

Such devices, in particular pen-type injectors are typically adapted to receive a replaceable or disposable cartridge containing and providing the medicament to be disposed by the device. The cartridge comprises an outlet to be coupled with a piercing element, e.g. an injection needle, cannula or the like in a fluid transferring way. Opposite to the distal dispensing end, the cartridge is typically sealed by way of a displaceable piston slidably arranged in the body of the cartridge. In order to expel a predefined dose of the medicament, a plunger or piston rod of a drug delivery device is adapted to act on the piston for displacing said piston by a predefined distance in distal, thus dose-dispensing direction.

On the one hand, the piston has to provide a durable and leak-proof seal in order to prevent any uncontrolled discharge of the medicament. On the other hand, the piston also has to prevent ingress of impurities or other external substances into the drug receiving volume of the cartridge. Apart from its sealing capability, the piston has to be displaceable with respect to the side walls of the cartridge. Friction forces inherently present at the contact surfaces of cartridge side walls and piston should be kept to a minimum to allow for an easy and smooth operation of the cartridge.

In particular when the device and/or its cartridge are used for the first time, the dosing accuracy may be suboptimal and hence crucial. Especially prior to an initial use of the device, its mechanically interacting components may not yet fully engage and/or mutual abutment of piston rod and piston of the cartridge is just obtained only during an initial distal displacement of the piston rod. In such situations, an initial dose dispensed by the device might be too small. Moreover, since the piston sealing the vitreous and tubular shaped body of the cartridge is of a comparatively elastic and compressible material, the piston itself may experience a respective compression in axial direction during an initial displacement of the piston rod. Such an initial compression may further sustain due to frictional forces between the inside facing side wall of the cartridge's body and the lateral or circumferential side wall or respective sealing lips of the piston.

Moreover, an eventual axial relaxation of the piston is rather disadvantageous and may effectuate an increase of a fluid pressure inside the cartridge. In situations where the cartridge is still in fluid connection with e.g. a piercing element, such internal pressure may lead to a post-dispensing droplet generation to be observed at a distal tip of the piercing assembly.

Document WO 2010/133675 A1 for instance discloses a bung for drug containing cartridges having a distal and a proximal end face. This bung also comprises at least two different materials, wherein a first material covers the whole lateral area of the bung and wherein a second material is at least partly arranged inside the bung. Furthermore, the first material has a larger compressibility than the second material.

Even though this bung provides a reduced axial compressibility, manufacturing of such a piston is cumbersome and cost-intensive since the second material is entirely surrounded by the first material. Manufacturing of such a bung may for instance require a multicomponent injection moulding process.

SUMMARY

It is therefore an object of the present invention to provide an improved piston for a cartridge to be used in a drug delivery device featuring a reduced degree of compressibility and which is beneficial in terms of dosing accuracy. Moreover, the piston should be easy to assemble in a cost-efficient way. The piston and the method to assemble the same should be further beneficial in respect of ensuring against product counterfeiting.

In a first aspect, the invention provides a piston for a cartridge to be filled with a medicament. The piston is to be placed as a proximal seal into a tubular shaped body of the cartridge in order to hermetically seal the inner volume of the cartridge. Moreover, the piston is adapted and designed to be displaced in a distal direction by means of a piston rod or by way of a comparable driving member of a drive mechanism of a drug delivery device in order to build up a respective fluid pressure inside the volume of the cartridge.

Typically, the cartridge features another but pierceable sealing member at a distal end by way of which the liquid medicament can be expelled from the cartridge in response to a distally directed displacement of the piston relative to the tubular body of the cartridge.

The piston comprises a first piston member comprising or made of a first material and forming a distal end face of the piston facing towards the inner volume of the cartridge. The piston further comprises a second piston member comprising a second material being of lower compressibility than the first material. Moreover, the second piston member is arranged in a cupped receptacle of the first piston member and forms a thrust receiving surface at a proximal end face of the piston.

In contrast to the embodiment as disclosed in WO 2010/133675 A1, the second piston member is directly adapted to become operably engaged with a thrust exerting member of a drive mechanism of a drug delivery device. Apparently, the proximally directed end face of the second piston member is accessible from outside the piston. The second piston member is therefore not entirely embedded or surrounded by the first piston member but is designed and adapted to directly engage with e.g. a piston rod of a drug delivery device. The second piston member at least partially provides a proximal end face of the piston.

Such an external accessibility of the proximal thrust receiving surface of the second piston member is beneficial in terms of dosing accuracy. A direct abutment and contact between a thrust exerting member, e.g. a piston rod and the second piston member featuring a comparatively low compressibility remarkably reduces axial compression of the piston, which may otherwise arise in particular in the course of an initial distally directed piston displacement.

Accessibility of the second piston member is further beneficial in terms of a manufacturing process of the piston. In effect, first and second piston members can be manufactured separately and require only mutual assembly prior to a final assembly of the piston inside the cartridge. Assembly of first and second piston members does not necessarily has to take place by way of injection moulding but may be conducted all-mechanically by way of a separate assembly process that takes place after the individual components, first and second piston member have been manufactured separately.

Moreover, a second piston member featuring pre-defined dimensions might be used with a large variety of first piston members featuring different mechanical or geometric properties depending on the particular cartridge the piston is to be assembled in. Additionally, it is conceivable, that a first piston member of pre-defined type and/or dimensions is to be coupled with a variety of different second piston members in order to modify the axial compressibility of the piston as a whole.

Since the second piston member comprises a material of lower compressibility compared to the first material, the second piston member may serve as a rigid core or as a stiffening component enhancing mechanical stiffness and rigidity of the piston while the rather elastic first piston member still provides an elasticity sufficient to seal the inner volume of the cartridge.

Moreover, the first and the second piston members may form or may constitute the entire piston. Hence, the piston, which is typically to be slidably arranged in a cartridge may consist of first and second piston members only, thereby forming or providing even a common proximal thrust receiving surface of first and second piston members to get in mechanical abutment with a thrust exerting piston rod or plunger of a delivery device.

In the present context the piston serves as a proximal seal of the cartridge and is to be assembled in the cartridge prior to delivery to the market and customers. Hence, a vitreous or polymer-based body of the cartridge and the piston assembled therein form a cartridge pre-configured to be operably connected with a driving mechanism by way of which the piston can be displaced with respect to the body of the cartridge for expelling a liquid medicament there from.

According to a preferred embodiment, the first and/or the second materials comprise a polymeric material.

Moreover, it is beneficial, when the first material comprises a natural and/or a synthetic rubber. Preferably, the first material comprises butyl rubber such like bromobutyl-rubber. In a further preferred embodiment, the second material comprises cyclic olefin copolymer (COC) featuring a mechanical compressibility being substantially smaller than the compressibility of the first material. In other words, the hardness or rigidity of the second piston member is substantially larger than that of the first piston member.

In particular, the first and the second materials may also substantially differ with respect to their specific weight. Since it is the first piston member only which forms the distal end face of the piston, the center of gravity of the entire piston can be axially displaced when making use of first and second materials for the first and second piston members featuring different specific weight. Especially in a mass production or mass assembly process such a displacement of the center of gravity may be of further use, e.g. for orienting a large number of pistons in a well-defined way. Preferably, the specific weight of the second piston member exceeds the specific weight of the first piston member by at least 5%, 10%, 15%, 20% or even by 30%.

It is of further benefit that, according to another embodiment, the first and/or the second piston members are of cylindrical or tubular shape and wherein the first piston member at least laterally embraces the second piston member. Moreover, since the first piston member forms the distal face of the piston, the first piston member also embraces and covers the distally directed end face of the second piston member. Preferably, the first piston member entirely receives the second piston member. Also, the second piston member preferably comprises a shape and geometry to entirely fill the receptacle provided in the first piston member. This way, any hollow space inside the receptacle of the first piston member can be substantially filled with rather rigid and non-compressible material.

In a further preferred embodiment, the second piston member buts with a bottom face of the first piston member in axial direction (z). It is of particular benefit, when a distally directed end face of the second piston member buts with a proximally directed bottom face of the receptacle of the first piston member. This way, the second piston member serving as a thrust transferring element directly contacts a distally positioned bottom face of the piston, which confines the inner volume of the cartridge with its oppositely located distally directed surface.

The piston according to the present invention comprises such a shape and geometry that a resulting axial displacement of second and first piston members is transferred in a dragging rather than pushing way to a proximally located sealing surface radially outwardly arranged at the circumference of the first piston member. Hence, a distally directed displacement of an annular sealing surface of the first piston member is predominately governed by dragging rather than pushing. The sealing surface therefore trails the movement of the thrust receiving surface of the second piston member. In effect, the annular circumferential side wall portion of the first piston member experiences an axial elongation rather than compression during a distally directed displacement. An axial compression can therefore be effectively counteracted.

Lateral side walls of the first piston member that may surround or embrace the second piston member are therefore no longer subject of axial compression during a distally directed displacement of a piston rod and/or of the second piston member. Axial compression may only take place in the bottom portion of the first piston member. It is then of particular benefit, that the bottom portion of the first piston member comprises an axial extension smaller than 20%, preferably smaller than 10% or even smaller than 5% of the total axial elongation of the piston and/or of the first piston member. By reducing the axial dimensions of the thrust transmitting bottom portion of the first piston member, total axial compression and/or relaxation of the piston can be kept at a rather low level.

In a further preferred embodiment, the thrust receiving surface of the second piston member is substantially flush-mounted with a proximal end face of the first piston member. This way, an even and/or flat proximal surface of the entire piston can be attained. However, it is also conceivable, that the thrust receiving surface of the second piston member is located axially offset compared to the proximal end face of the first piston member. The second piston member may axially protrude from the first piston member in proximal direction or it may be located entirely inside the cupped receptacle of the first piston member.

Depending on the lateral dimension and overall geometry of a piston rod, a protruding, recessed or flush-mounted arrangement of first and second piston members at the proximal end face of the piston may be preferred.

In another embodiment, the first piston member is press-fitted in the first piston member. Mutual assembly of first and second piston members can for instance be attained by an all-mechanical press-fitting assembly step, wherein for instance the second piston member is squeezed inside the cupped receptacle of the first piston member. Moreover, also the first and surrounding piston member may be pulled or put over the rigid second piston member. Here, first and second piston members may be kept and secured in an assembly configuration by mechanical restoring forces arising from an elastic deformation of first and/or second piston member when mutually assembled.

In this context it is also conceivable that first and second piston members frictionally engage at least when the second piston member is disposed in the cupped receptacle of the first piston member. Additionally or alternatively, first and second piston members may also be mutually interconnected by means of an adhesive to be applied onto at least one of the contact surfaces of the first and/or the second piston member.

For inserting the second piston member into the cupped receptacle of the first piston member it is of particular benefit when the cupped receptacle of the first piston member is of cylindrical shape to smoothly receive the second piston member.

It is generally also conceivable to achieve a bonded and non-separable interconnection of first and second piston members by way of injection moulding. Hence, at least the second piston member may be injection moulded into the cupped receptacle of the first piston member, thereby serving as a mould. In the course of an injection moulding process a mutual bonding of mutually abutting inner and outer side wall sections of first and second piston members can be attained.

Mutual assembly of two separate components of the piston is further beneficial for integration of further components into the piston, such like an electronic circuit. Hence, according to another preferred aspect, an electronic circuit may be arranged between first and second piston members, preferably between mutually abutting bottom face of the first piston member and a distally directed end face of the second piston member. However, since said bottom and distal end face of first and second piston members are adapted to transfer axially directed thrust it may be of further benefit, when according to another embodiment distal end face of the second piston member and/or bottom face of the first piston member comprise at least one recess to at least partially receive the electronic circuit. This way, the electronic circuit can be effectively protected from mechanical impact arising in the interface of first and second piston members.

The electronic circuit is preferably designed as a microchip and may comprise a data storage at least providing manufacturing date and/or time. Moreover, the electronic circuit may be equipped with different types of sensors, like temperature, pressure- or light-sensitive sensors in order to detect whether the piston and/or the associated cartridge has been exposed to inadmissible environmental conditions. The electronic circuit may be further equipped with a communication unit, preferably with a wireless communication unit by way of which the content of stored data can be retrieved on demand.

For instance, the electronic circuit may be comprise a RFID element allowing to communicate with a corresponding reading device in a wireless way. This way, counterfeited cartridges and pistons can be easily detected. Additionally, the anti-counterfeiting electronic circuit can be entirely covered by first and second piston members and is therefore not visible to a user or dealer.

In still another embodiment, the second piston member comprises an axial elongation of at least 80%, 90% or preferably of even up to 95% of the total axial elongation of the piston. By maximizing the axial elongation of the second piston member, axial compressibility of the entire piston can be further reduced. Maximization of axial elongation of the second piston member is only limited by the sealing properties of the bottom portion of the first piston member.

Hence, axial elongation of the corresponding bottom portion of the first piston member may only be reduced to such a minimum in which a sufficient sealing can be still provided.

In a further independent aspect the invention also relates to a cartridge to be used with a drug delivery device and comprising a tubular shaped body confining an inner volume at least partially filled with a medicament and being sealed by a piston as described above. Hence, the piston of said cartridge comprises first and second piston members, wherein the second piston member features a lower compressibility than the first piston member.

In a further independent aspect, the invention also relates to a method of manufacturing a piston as described above. The method of manufacturing comprises the steps of providing a first piston member having a first material and comprising a cupped receptacle which is open towards a proximal end thereof. In a second step, a second piston member made of a second material and featuring a lower compressibility compared to the first material is inserted into the cupped receptacle, wherein the second piston member comprises a proximal end face forming a thrust receiving surface at a proximal end of the piston.

Depending on the types of materials used for first and second piston members, various different ways of mutual assembly are generally conceivable. First and second piston members may for instance be press-fitted. Alternatively, the piston having two piston members of different material may also be manufactured by way of injection moulding or by way of bonding.

In a further preferred embodiment, an electronic circuit is positioned in the receptacle of the first piston member and/or in a distally directed recess of the second piston member prior to insertion of the second piston member in said receptacle of the first piston member. In effect, the mutual mechanical assembly of first and second piston members is beneficial for assembling or embedding the electronic circuit between the first and second piston members in a region being non-visible in the finally assembly of the piston.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-H2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the aforementioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and ε have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a preferred embodiment of the invention will be described by making reference to the drawings, in which.

DETAILED DESCRIPTION

Figure 1:
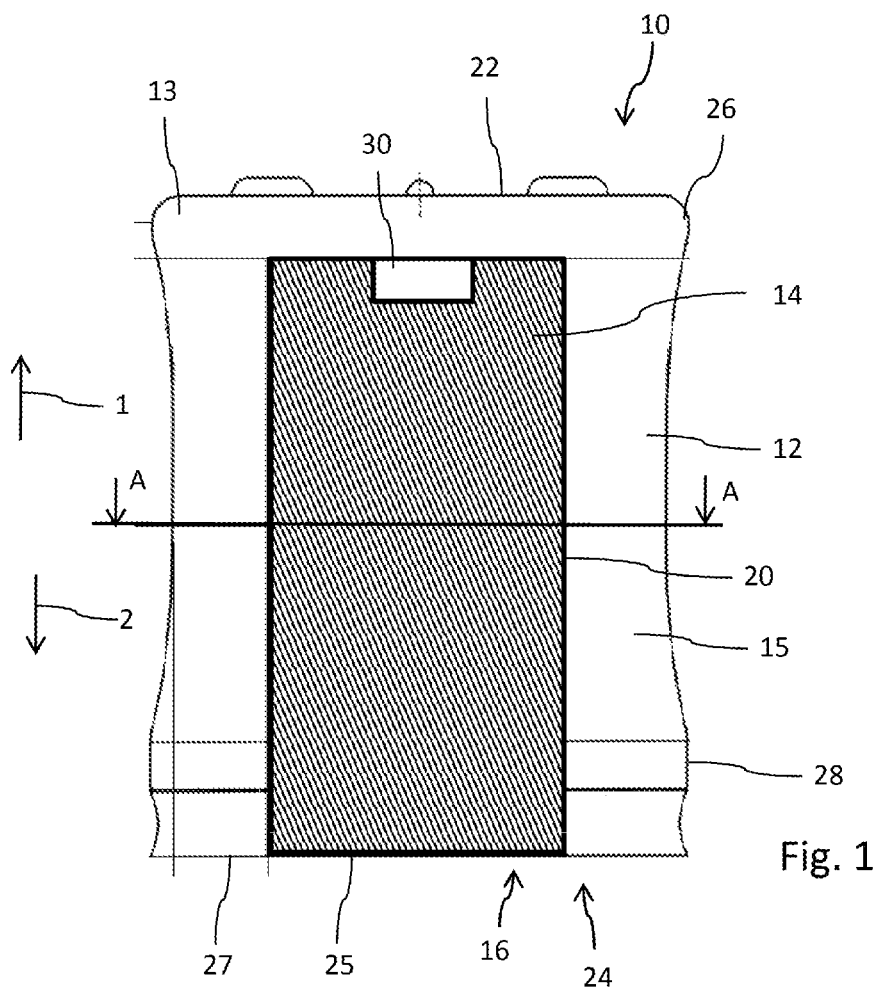
FIG. 1 schematically illustrates a cross-sectional side view of the piston.
Figure 2:
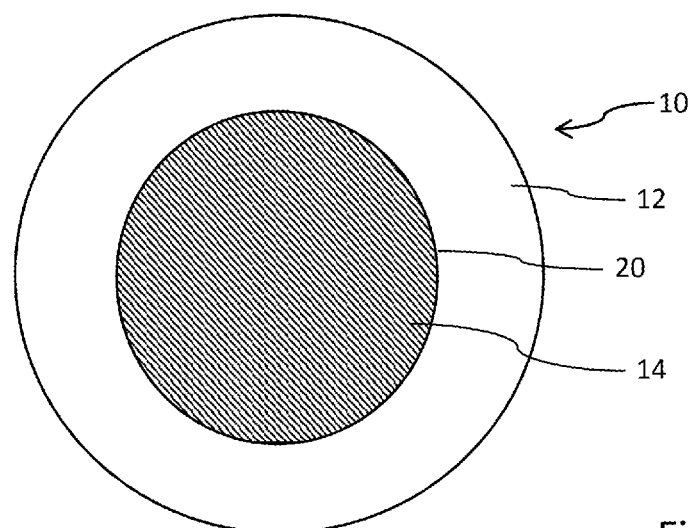
FIG. 2 is indicative of a lateral cross section of the piston according to FIG. 1 along A-A and FIG. 3 shows a typical cartridge design.

The piston 10 as illustrated in FIGS. 1 and 2 comprises two components, namely an outer and circumferential first piston member 12 and an inner second piston member 14 that serves as a rigid core to provide reduced axial compressibility of the entire piston 10. The first piston member 12 typically made of bromobutylene-rubber or chlorobutylene-rubber and thereby featuring a comparatively large mechanical compressibility has a cupped receptacle 16 of substantially cylindrical shape which is accessible from the proximal end of the piston 10.

Figure 3:
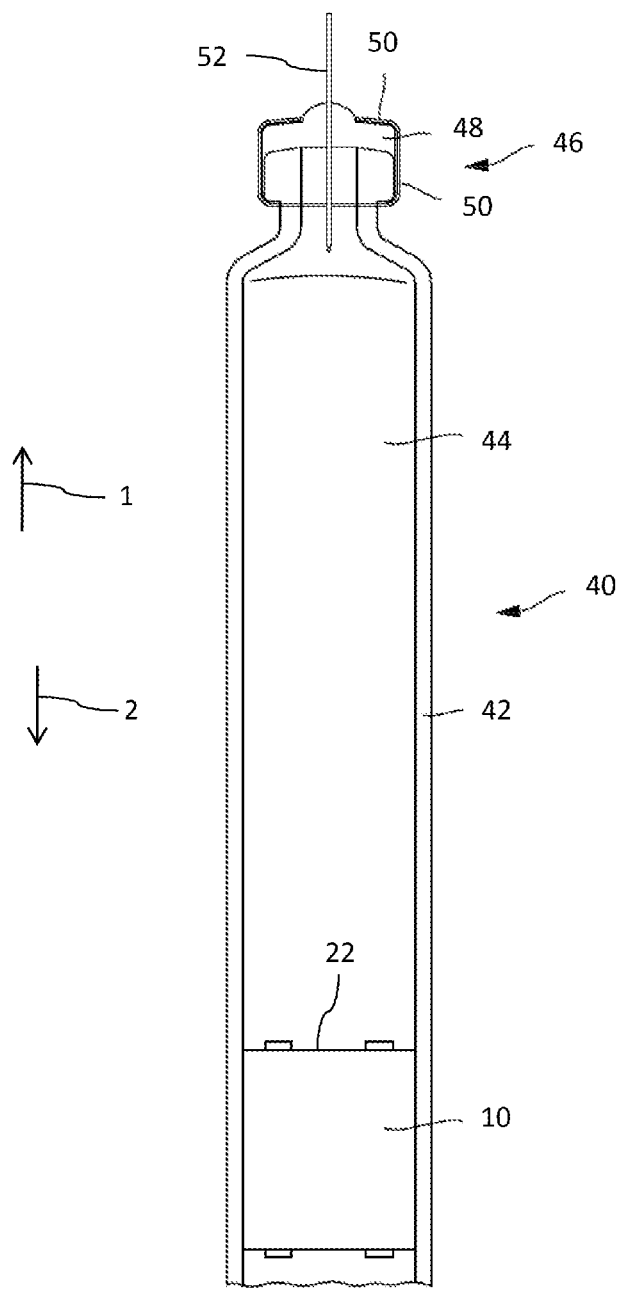

In the present context, distal direction 1 points towards the inner volume of a cartridge 40 which is for instance shown in FIG. 3. The opposite proximal direction 2 points towards a thrust exerting mechanical component, such like a piston rod which is not explicitly shown. The piston 10 as illustrated in FIG. 1 therefore comprises a distal end face 22 which may get in direct contact with the inner volume of the cartridge 40 and hence with the liquid medicament. The opposite end face 24 is in turn adapted to act as a thrust receiving surface and to get in direct contact with a thrust exerting mechanical component of e.g. with a piston rod of a drive mechanism of a drug delivery device.

The cupped receptacle 16 of the first piston member 12 is entirely filled with the second piston member 14 featuring a lower compressibility than the material of the first piston member 12. This way, the second piston member 14 provides enhanced mechanical rigidity and stability and therefore reduces axial compressibility of the piston 10 when the piston 10 is subject to distally directed thrust acting on the proximal end face 24. The second piston member 14 may comprise a polymeric material such a COC having a lower compressibility than the material used for the first piston member 12. First and second piston members 12, 14 are for instance frictionally engaged. The lateral side wall of the cylindrically-shaped second piston member 14 is gets in direct and frictional contact with the inside facing side wall 20 of the first piston member 12.

Moreover as indicated in FIG. 1, a proximally located end face 25 of the second piston member 14 is flush-mounted with a proximal end face 27 of the first piston member 12. This way, proximal end faces 25, 27 of second and first piston members 14, 12 mutually complement to provide a substantially flat and even shaped proximal thrust receiving surface 24 of the piston 10. In alternative embodiments, the proximal end face 25 of the second piston member 14 may proximally protrude from the first piston member or may also be recessed in distal direction 1.

It is of further benefit, when the radial dimension of the second piston member 14 mates and corresponds with a thrust exerting distal component of a piston rod or with a comparable drive member of a drug delivery device. This way, distally directed thrust can be entirely transferred to the second piston member 14 which is adapted to transfer a respective thrust to an inward facing bottom surface 18 of a bottom portion 13 of the first piston member 12. Consequently, externally applied distally directed thrust can be directly transferred to the bottom portion 13 of the first piston member 12, which due to its reduced axial dimensions compared to the axial dimensions of the second piston member 14, may then only be subject of an almost insignificant axial compression.

The lateral side wall section 15 of the first piston member 12 may only be subject of an axially directed tension or drag force. In effect, the side wall 15 may no longer be subject to axial compression.

The first piston member 12 may further comprise distally and/or proximally located sealing lips 26, 28 which extend radially outwardly and which are adapted to frictionally engaged with the inside facing side walls of the cartridge's body.

As further illustrated in FIG. 1, at least one electronic circuit 30 may be arranged in the interface region between first and second piston members 12, 14. For this purpose, either the first piston member 12 and/or the second piston member 14 may comprise a recess to receive the electronic circuit 30, which by its arrangement between the piston members 12, 14 is not visible from outside.

However, the electronic circuit 30 may be equipped with wireless communication means, such like an RFID element allowing to read out genuine information about the piston and/or the cartridge. This way, an effective anti-counterfeiting means can be implemented into a piston 10 in a substantially non-visible way.

As further illustrated in FIG. 3, the piston 10 typically serves as a proximal seal confining an inner volume 44 of a cartridge 40. The piston 10 is slidably positioned in a tubular shaped body 42 of the cartridge. Near a distal end the cartridge 40 comprises a bottle-necked outlet end 46. There, another but pierceable seal 48 is provided that acts as a septum. The seal 48 is kept in position by way of a beaded cap 50. The septum 48 is intended to be pierced by a a double tipped needle 52 to dispense a predefined dose of the medicament e.g. into biological tissue.

The invention claimed is:

1. A piston for a cartridge to be filled with a medicament, the piston comprising:
    a first piston member comprising a first material and forming a distal end face of the piston,
    a second piston member comprising a second material of lower compressibility compared to the first material,
    wherein the second piston member is arranged in a cupped receptacle of the first piston member and providing a thrust receiving surface at a proximal end of the piston, characterized by an electronic circuit arranged between a proximally directed bottom face of the first piston member and a distal end face of the second piston member, wherein the proximally directed bottom face of the first piston member and the distal end face of the second piston member mutually abut, and wherein the distal end face of the second piston member and/or the proximally directed bottom face of the first piston member comprise a recess to receive the electronic circuit.

2. The piston according claim 1, wherein first and/or second materials comprise a polymeric material.

3. The piston according to claim 1, wherein the first material comprises a natural and/or a synthetic rubber.

4. The piston according to claim 1, wherein the second material comprises cyclic olefin copolymer (COC).

5. The piston according to claim 1, wherein the first and/or the second piston member are of cylindrical or tubular shape and wherein the first piston member laterally embraces the second piston member.

6. The piston according to claim 1, wherein the second piston member buts with the proximally directed bottom face of the first piston member in axial direction.

7. The piston according to claim 1, wherein the thrust receiving surface of the second piston member is flush-mounted with a proximal end face of the first piston member to form an even or flat shaped proximal surface of the piston.

8. The piston according to claim 1, wherein the second piston member is press-fitted in the receptacle of the first piston member.

9. The piston according to claim 1, wherein the second piston member comprises an axial elongation of at least 80%, 90% or at least 95% of the total axial elongation of the piston.

10. A cartridge to be used with a drug delivery device comprising a tubular shaped body confining a inner volume at least partially filled with a medicament and being sealed by a piston according to claim 1 being displaceably arranged in the tubular body in axial direction.

11. A method of manufacturing a piston according to claim 1, comprising the steps of:
   providing a first piston member of a first material and having a cupped receptacle,
   inserting a second piston member of a second material of lower compressibility than the first material into the receptacle, and
   arranging an electronic circuit in the receptacle of the first piston member or in a recess of the second piston member prior to insertion of the second piston member in the receptacle of the first piston member.

* * * * *